United States Patent [19]
Blecher

[11] Patent Number: 5,840,504
[45] Date of Patent: Nov. 24, 1998

[54] METHOD FOR SEPARATING SEX SPECIFIC MOLECULES AND NON-SEX SPECIFIC MOLECULES

[75] Inventor: Stan R. Blecher, Guelph, Canada

[73] Assignee: University of Guelph, Guelph, Ontario, Canada

[21] Appl. No.: 694,784

[22] Filed: Aug. 9, 1996

Related U.S. Application Data

[60] Provisional application No. 60/002,193 Aug. 11, 1995.

[51] Int. Cl.[6] .......................... G01N 33/536; C07K 16/28
[52] U.S. Cl. ........................................ 435/7.21; 530/389.1
[58] Field of Search .......................... 435/7.21; 530/389.1

[56] References Cited

U.S. PATENT DOCUMENTS

| | | |
|---|---|---|
| 4,085,205 | 4/1978 | Hancock . |
| 4,191,749 | 3/1980 | Bryant . |
| 4,448,767 | 5/1984 | Bryant . |
| 4,722,887 | 2/1988 | Fabricant et al. . |
| 4,999,283 | 3/1991 | Zavos et al. . |
| 5,021,244 | 6/1991 | Spaulding . |
| 5,346,990 | 9/1994 | Spaulding . |

FOREIGN PATENT DOCUMENTS

| | | |
|---|---|---|
| 0 205 293 | 12/1986 | European Pat. Off. . |
| 2070641 | 2/1980 | United Kingdom . |
| WO/91/17188 | 11/1991 | WIPO . |

OTHER PUBLICATIONS

Eichwald and Silmser, Transplant Bull, 2:148, 1955.
Watchel et al., Nature, 257:235, 1975.
Shalev et al., J. Immunogentics, 5:203, 1978.
Muller et al., Nature, 280:142, 1979.
Bradley et al., Hum. Genet. 76:352, 1987.
Brunner and Wachtel, J. Immunol. Methods 106:49,1988.
Epstein et al., Tiss.Antigens 15:63, 1980.
Anderson, Theriogenology, 27:81, 1987.
Wachtel et al., Fert. Ster., 50:355, 1988.
Avery and Schmidt, Acta. Vet. Scand., 30:155, 1989.
de Lima et al., Theriogenology, 39:1343. 1993.
Utsumi et al, Mol. Reprod. Devel., 34:25, 1993.
Coe, Proc. Natl. Acad. Sci., 74:730, 1977.
Brown et al., Nature, 349:38, 1991.
Windsor et al., Reprod. Fert. Dev. 5:155, 1993.
Utsumi et al., Mol. Reprod. Devel., 36:238, 1993.
Olsaker et al., Anim. Genet, 24:311, 1993.
Ali et al., Archives of Andrology, 24:235, 1990.
Goldberg et al., Nature, 232:478, 1971.
Peter et al., Theriogenology, 40:1177, 1993.
Cartwright et al., Mol. Reprod. Dev., 34:323, 1993.
Simpson et al., Nature, 326:876, 1987.

*Primary Examiner*—Frank C. Eisenschenk
*Assistant Examiner*—Evelyn Rabin
*Attorney, Agent, or Firm*—Merchant, Gould, Smith, Edell, Welter & Schmidt

[57] ABSTRACT

A method for identifying non-sex specific and sex specific molecules associated with animal cell membranes is described. The method involves preparing a cell membrane fraction from adult, fetal, or embryonic animal cells; treating the cell membrane fraction with one or more substances which bind to non-sex specific molecules in the cell membrane fraction to form conjugates between the non-sex specific molecules and the substances; separating the material in the cell membrane fraction which does not bind to the substances to obtain a subfraction containing sex specific molecules; optionally, removing the substances in the conjugates to obtain a subfraction containing non-sex specific molecules; and, isolating the sex specific molecules and optionally non-sex specific molecules in the subfractions. Sex specific and non-sex specific molecules and methods of using the sex specific and non-sex specific molecules for sexing are also described.

7 Claims, 1 Drawing Sheet

FIGURE 1

METHOD FOR SEPARATING SEX SPECIFIC MOLECULES AND NON-SEX SPECIFIC MOLECULES

The present application claims priority under 35 U.S.C. 119(e) from the provisional patent application, application Ser. No. 60/002,193, filed Aug. 11, 1995, now abandoned.

FIELD OF THE INVENTION

The invention relates to a novel method for identifying sex specific and species specific molecules, molecules identified using the method, and uses of the molecules.

BACKGROUND OF THE INVENTION

There is a great interest in controlling the sex of mammalian offspring, and there have been numerous proposals for methods of preselecting sex. The impetus for controlling sexing has been provided by the desire to reduce the incidence of sex-linked genetic disorders, and by more efficient agricultural production. In the case of the latter, the bovine dairy and beef sectors of agriculture require female and male animals respectively; in each case, the unwanted sex animal is simply culled, resulting in great loss of materials.

Two approaches are currently being actively pursued for sex selection in mammals: sexing (i.e. establishing the genetic sex) of preimplantation embryos, and X and Y bearing spermatozoa separation. Sexing of preimplantation embryos has been accomplished by (a) karyotyping, (b) by polymerase chain reaction (PCR) amplification of Y-chromosome specific nucleotide sequences, or (c) by immunological methods. The first two methods suffer from the disadvantage that they involve embryo micromanipulation in order to obtain biopsies and therefore they are "invasive" procedures.

The alternative immunological methods are based on immunodetection of a male-typical molecule. Studies on male-typical molecules commenced with the discovery by Eichwald and Silmser (1955, Transplant Bull 2:148) of what is now known as the H-Y antigen. These authors found that within the inbred mouse strain C57BL/6, skin transplants from males to females were rejected, whereas transplants from males to males, females to males and females to females within the same strain were tolerated. Hauscha (1955, Transplant Bull 2:154) postulated that these data could be explained by an antigen coded for by a Y-linked gene, and the system came to be known as H-Y (histocompatibility locus on the Y chromosome).

H-Y is a "minor" histocompatibility antigen, the genetic locus of which is separate from the major histocompatibility complex (MHC). Minor histocompatibility loci are mainly concerned with cellular immunity; few if any products of these loci are efficient in raising antibodies. Nevertheless, a search for a serological counterpart to the transplantation H-Y antigen appeared to have been successful when a serological "H-Y" method was reported by Goldberg et al.(1971, Nature 232: 478).

New evidence has indicated that the serological detectable "H-Y" antigen may not be the same as the histocompatibility antigen. In particular, serological and transplantation H-Y were shown to be coded for by genes at different loci (Simpson et al., 1990, Arch. Androl. 24:235). The molecule identified by serological methods is now widely referred to as serologically detectable male antigen (SMA). It was also demonstrated by means of absorption, that rodent anti H-Y antisera cross-react with female tissues or cells of birds (Watchel et al. 1975, Nature 257:235; Shalev et al., 1978, J. Immunogentics 5:203; Muller et al., 1979, Nature 280:142), the female bird being the heterogametic sex. Thus, the serological factor characterizes the heterogametic sex rather than the male sex.

H-Y antibodies were and continue to be used in sexing studies. The early techniques for serological study of H-Y, which depended, to a certain extent, on subjective assays, were improved upon by development of enzyme-linked immunoabsorbent assay (ELISA) methods by Bradley et al. (1987, Hum. Genet. 76:352) and Brunner and Wachtel (1988, J. Immunol. Methods 106:49). Other advances led to partial success in sexing embryos (Epstein, 1980, Tiss. Antigens 15:63; Anderson, 1987, Theriogenology 27:81; Wachtel, 1988, Fert. Ster. 50:355; Avery and Schmidt, 1989, Acta. Vet. Scand. 30:155). Recent immunological sexing studies appear to be achieving approximately the same rates of success as the above-mentioned work. For example, de Lima et al (1993, Theriogenology 39:1341) report 83% success in sexing murine and bovine embryos, using polyclonal and monoclonal antibodies. Utsumi et al. (1993, Mol. Reprod. Devel. 34:25) applied H-Y antibody to embryos of various species maintained in culture. Development was arrested in approximately half, and of the cattle embryos so arrested, close to 80% had XY karyotype, while 80–90% of those unaffected were XX. Utsumi and Iritani (1993, Mol. Reprod. Devel. 36:238) found that of 35 cattle blastocysts sexed by H-Y antibody the diagnosis in 31 cases (89%) agreed with the diagnosis made by DNA analysis.

Coe (1977, Proc. Nat. Acad. Sci. 74: 730) has identified a "female protein" which is hormone-dependent and hence unlikely to be found in blastocysts or sperm. Brown et al. (1991, Nature 349: 38) reported the first XX-specific molecule, an mRNA molecule transcribed by the "inactivated" X, and therefore only produced in females in somatic tissues.

Many techniques have been investigated for the separation of X- from Y-chromosome-bearing sperm in mammals. Some techniques have been based on the characteristics of the sperm e.g. size, head shape, mass, surface properties, surface macromolecules, DNA content, swimming velocity, and motility (see review by Windsor et al., 1993, Reprod. Fert. Dev. 5:155). Attempts to sex sperm by immunological methods using H-Y antibody have also been made (e.g. U.S. Pat. Nos. 4,448,767 and 4,191,749 to Bryant). Other authors found no evidence that H-Y is preferentially expressed on Y-bearing sperm (e.g. Hendricksen et al. 1993, Mol. Reprod. Devel. 35:189) and, in a review, Windsor et al. (1993, Reprod. Fert. Dev. 5:155) have concluded that no differences between the two classes of sperm can be detected immunologically.

Fabricant et al., (U.S. Pat. No. 4,722,887), describes a method for separating X- and Y-sperm by polymeric phase separation based on differential expression of a sperm cell-surface sulfoglycolipid.

Spaulding, (U.S. Pat. No. 5,021,244) describes a method for sorting sperm into enriched X- and Y-chromosome bearing preparations. Spaulding uses DNA content and cell sorting techniques to separate the subpopulations. However, the former technique may introduce changes to the DNA, and the latter technique is not very accurate since there is only about a 3% difference in DNA content between X- and Y-sperm. Further, Spaulding assumes that the subpopulations are enriched for each type of sperm, but Spaulding does not check that each of the separated groups of sperm are in fact X-sperm and Y-sperm.

SUMMARY OF THE INVENTION

The present inventor has developed a method for identifying sex-specific molecules (SSMs) which are present on the surface of adult, fetal, and embryonic animal cells. The method utilizes xenogeneic immunization to produce antibodies to non-sex specific antigens. The antibodies to the non-sex specific antigens are used to remove non-sex specific components of antigenic material and thus to enrich the antigenic material for residual sex-specific molecules. The sex-specific material, after purification, is then used to raise xenogeneic opposite-sex (female anti-male or male anti-female) antibodies.

The method in utilizing xenogeneic immunization produces a more vigorous antibody response than isogeneic, intraspecies immunization, with the result that both the avidity of the antigen-antibody binding, and the titres of antibody in the antisera are improved. Hitherto species-specific antibodies which interfered with recognition of the sex-specific antibodies in SMA antisera were widely considered to be an insuperable problem of using xenogeneic immunization.

The present inventor has used his method to identify both male and female specific molecules. The isolation of male and female specific molecules permits the preparation of significant quantities of antibodies with high affinity. These antibodies have utility in sexing of animal cells and tissues, and will provide non-invasive methods for sexing that have both high specificity (i.e. give few false positives) and high sensitivity (give few false negatives).

The present inventor has also used the method to identify non-sex specific molecules (also referred to herein as species specific molecules), which, for example, may be used as species specific allelic markers.

Broadly stated the present invention relates to a method for identifying sex specific molecules and non-sex specific molecules associated with animal cells for example with animal cell membranes, preferably plasma membranes (outer membranes) comprising (a) treating a cell membrane fraction from adult, fetal, or embryonic animal cells, with one or more substances which bind to non-sex specific molecules in the cell membrane fraction to form conjugates between the non-sex specific molecules and the substances;

(b) separating the material in the cell membrane fraction which does not bind to the substances to obtain a subfraction containing sex specific molecules;

(c) isolating the sex specific molecules in the subfraction; and (d) optionally, separating the substances from the conjugates to obtain a second subfraction containing non-sex specific molecules and isolating the non-sex specific molecules from the second subfraction.

In an embodiment of the invention the substance is an antibody against non-sex specific molecules, and in a preferred embodiment the substance is female anti-female antibody and/or male anti-male antibody.

The sex specific molecules and non-sex specific molecules identified using the method of the invention may be used to identify nucleic acid molecules having sequences which encode sex specific and non-sex specific molecules. Therefore, in accordance with an embodiment of the invention a purified and isolated nucleic acid molecule is provided containing a sequence encoding a sex specific molecule identified using the methods of the invention. In accordance with another embodiment of the invention a purified and isolated nucleic acid molecule is provided containing a sequence encoding a non-sex specific molecule identified using the methods of the invention.

The nucleic acid molecules encoding sex specific and non-sex specific molecules, or fragments thereof may be inserted into an appropriate expression vector, i.e. a vector which contains the necessary elements for the transcription and translation of the inserted protein-coding sequence. Accordingly, recombinant DNA molecules adapted for transformation of a host cell may be constructed which comprise a nucleic acid molecule encoding a molecule identified using the methods of the invention, and one or more transcription and translation elements operatively linked to the nucleic acid molecule.

The recombinant molecule can be used to prepare transformed host cells expressing the molecule, or part thereof encoded by a nucleic acid molecule of the invention. Therefore, the invention further provides host cells containing a recombinant molecule of the invention.

The invention further provides a method for preparing a sex specific molecule, a non-sex specific molecule, or isoforms or parts thereof utilizing the purified and isolated nucleic acid molecules identified using the methods described herein.

The invention further broadly contemplates a purified and isolated sex specific molecule or non-sex specific molecule identified using the methods described herein.

In accordance with a preferred embodiment of the invention, a sex specific molecule is provided which is characterized as (a) male specific; (b) associated with the plasma membrane of cells from bovine fetal and adult tissues, particularly the testes, spleen and kidneys; and (c) having a molecular weight of about 60 KD.

The sex specific and non-sex specific molecules identified using the methods of the invention, or isoforms or parts thereof, may be conjugated with other molecules, such as proteins, polypeptides, or they may be glycosylated.

The invention also permits the construction of nucleotide probes which are unique to the nucleic acid molecules encoding the sex specific and non-sex specific molecules identified using the method of the invention and accordingly to the sex specific and non-sex specific molecules, or isoforms, or parts thereof. Thus, the invention also relates to a probe comprising a nucleotide sequence coding for a sex specific molecule or a non-sex specific molecule identified using the methods of the invention. The probe may be labelled, for example, with a detectable substance and it may be used to select from a mixture of nucleotide sequences a nucleotide sequence coding for a sex specific molecule, a non-sex specific molecule, or parts thereof.

The molecules identified using the method of the invention, which are isolated from tissues or recombinantly produced, may be used to prepare antibodies. The invention therefore further contemplates antibodies having specificity against an epitope of a sex specific molecule or a non-sex specific molecule identified using the methods of the invention, or an isoform or part of the molecule. Antibodies may be labelled with a detectable substance and they may be used to detect a sex specific molecule or a non-sex specific molecule in samples from tissues, cells, and embryos.

The sex specific antigens identified using the methods described herein and antibodies against an epitope of such a sex specific molecule, may be used to increase the probability that offspring will be of a desired sex, or that they will or will not carry a gene for a sex-chromosome linked trait.

The antibodies against an epitope of a sex specific molecule identified using the methods of the invention are useful for differentiating between males and females, based on the determination of the presence of the sex specific molecule associated with a cell membrane, preferably the plasma membrane. Therefore, the invention also contemplates a method for differentiating between males and females comprising exposing an embryo or growth media of an embryo to one or more antibodies specific for an epitope of a sex specific molecule identified using the methods of the invention, under conditions so that a conjugate forms between the antibody and the sex specific molecule, and detecting the conjugates. The detection of a conjugate with antibody to a male specific molecule determines a male, and the detection of a conjugate with antibody to a female specific molecule determines a female.

The present inventor has found that sperm carry sex specific molecules identified using the method of the invention. Therefore, the invention contemplates a method for separating male and female determining sperm from native semen which comprises treating the native sperm with one or more antibodies against a sex specific molecule identified using the methods of the invention, to form conjugates between male or female determining sperm and the antibodies, and isolating the conjugates, and sperm which have not bound to antibodies.

Still further, the invention contemplates immunizing females against X-sperm, Y-sperm, or both by administering an immunogenic amount of a sex specific molecule identified using the methods of the invention thereby increasing the probability of offspring of a certain sex, or decreasing fertility. Antibodies against an epitope of a sex specific molecule of the invention, and complement may also be used to kill male and/or female embryos in vitro or in vivo. In particular, antibodies against an epitope of a sex specific molecule of the invention, and complement may be placed in the uterus of a pregnant animal to kill male and/or female embryos.

Antibodies against an epitope of a sex specific molecule identified using the methods of the invention may also be conjugated with a cytotoxin which inactivates sperm.

The sex specific molecules identified using the methods of the invention may also be used to detect the presence of antibodies specific for the sex specific molecules in a sample.

The non-sex specific molecules identified using the methods described herein and antibodies against an epitope of such non-sex specific molecules, may be used as species specific allelic markers. For example, the molecules and antibodies may be used to detect contamination of tissue culture with an unidentified cell, and they may be used in somatic cell studies to identify human and/or murine chromosomes.

The invention also relates to kits useful in performing the methods of the invention comprising antibodies against epitopes of sex specific molecules, or non-sex specific molecules identified using the methods of the invention, and suitable supports useful in performing the methods of the invention.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DESCRIPTION OF THE DRAWINGS

The invention will be better understood with reference to the drawing in which.

DETAILED DESCRIPTION OF THE INVENTION

I. METHOD OF IDENTIFYING SPECIES AND SEX SPECIFIC MOLECULES

As hereinbefore mentioned, the present invention relates to a method for identifying sex specific molecules and non-sex specific molecules associated with animal cells preferably membranes, more preferably plasma membranes. One skilled in the art would appreciate that other molecules may be identified using the method of the invention. The molecules identified using the method of the invention, in particular sex specific and non-sex specific molecules, include glyco-, lipo-, and phosphoproteins, polypeptides, and peptides and complexes of these molecules.

The method described herein may be applied to any animals in which there is sufficient evolutionary conservation of sex specific alleles, and it can accordingly be applied to a wide variety of animals. For example, it may be applied to mammals, avian species, reptiles, and fish, preferably, commercially important mammalian species including cattle, dogs, cats, horses, swine, and sheep. It is also applicable to humans.

The method involves first preparing a tissue sample from adult, fetal, or embryonic animal cells or tissues. Samples may also be prepared from parthenogenotes. The tissue sample is preferably obtained from a cell membrane, for example, the plasma membrane (outer membrane), inner membrane, mitochondrial membrane, and endoplasmic reticulum membrane, most preferably the plasma membrane. Tissue samples may be obtained using conventional methods known to those skilled in the art. For example, a plasma membrane fraction may be obtained as follows. Organs such as spleen, kidneys, testes, and ovaries may be dissected out of bovine fetal or adult tissue, placed in a homogenization buffer, containing protease inhibitors and solubilization agents such as detergents, and cut into very small pieces using fine scissors. DNAase may be added and the tissue may be homogenized using for example, a Polytron™ homogenizer. The homogenate may be gently layered onto a sucrose solution and ultracentrifuged at 900×g, at 4° C. for 60 minutes. Plasma membrane material can be recovered as an interfacial band, washed by further ultracentrifugation, and then stored frozen until needed.

In an embodiment of the invention, sex specific molecules associated with the membrane of sperm, preferably the plasma membrane of sperm, are isolated. A cell membrane fraction may be obtained from sperm preparations by first preparing X and Y enriched sperm fractions. The enriched fractions may be prepared based on the characteristics of the X- and Y-sperm e.g. size, head shape, mass, surface properties, surface macromolecules, DNA content, swimming velocity, and motility (See review by Windsor et al., 1993, supra). In one embodiment, the sperm preparations are subjected to flow cytometry which is based on the fact that X sperm contain more DNA than Y sperm and the X-sperm show a slightly brighter fluorescence than the Y-sperm after treatment with a DNA-binding fluorescent stain (Hoechst 33342). In another embodiment, the sperm preparations are treated with anti-male or female embryo or fetal antibodies.

Membrane vesicles may be isolated from the enriched X and Y fractions using cavitation (See for example, Gillis et al., Prep. Biochem., 8, pp.363–378, 1978). Cell membrane vesicles consisting substantially of head cell membrane and some tail cell membrane from sperm heads, tails and other particulates may then be obtained by pelleting centrifugation, preferably centrifugation twice at 2500×g for about 30 minutes. The supernatant containing the cell membrane constituents may then be centrifuged (e.g. 100,000×g) to obtain the material to be used in the method of the invention. The material may be resuspended and washed in tris acetate (10 mM, pH 5.5) to remove any fluorescent stain.

The membrane fraction obtained as described above, is treated with one or more substances which bind to non-sex specific molecules in the fraction to form conjugates between the non-sex specific molecules and the substances. In an embodiment of the invention, the substance is an antibody against non-sex specific molecules, and in a preferred embodiment the substance is female anti-female antibody and/or male anti-male antibody prepared by xenogeneic immunization. For example, male and female animals of a first species (designated "SPF") are immunized with male and female cell membrane fractions isolated from a second animal species (designated "SP2") to produce male SP1 anti-female SP2 antibodies, male SP1 anti-male SP2 antibodies, female SP1 anti-male SP2 antibodies, and female SP1 anti-female SP2 antibodies. The first and second animal species are selected so that there is sufficient evolutionary conservation of sex specific alleles, i.e. they are selected so that an SP1 animal does not substantially produce antibodies to the sex specific molecules of an SP2 animal of the same sex.

The first and second animal species may be selected from rabbits, sheep, rats, mice, horses, cows, and goats, or non-mammalian species such as various fowl. In an embodiment of the invention, male and female rabbits are immunized with male and female bovine plasma membrane fractions to produce male rabbit anti-female bovine antibodies, male rabbit anti-male bovine antibodies, female rabbit anti-male bovine antibodies, and female rabbit anti-female bovine antibodies.

The female anti-female antibody and male anti-male antibody preparations prepared by xenogeneic immunization as described herein may be further treated to ensure that the preparations do not contain any antibodies to female sex specific molecules and male sex specific molecules, respectively. For example, a male rabbit anti-male bovine antibody preparation may react with a male bovine plasma membrane fraction to obtain conjugates containing the antibodies in the preparation and the antigens in the fraction. The antigens now bound to the male rabbit anti-male bovine antibodies may be isolated and used to immunize a female rabbit. The female rabbit anti-male bovine antibodies may then be treated with a female bovine plasma membrane fraction. Anti-male bovine sex specific molecules will not bind to antigens in the female bovine plasma membrane fraction, while the anti-male bovine non-sex specific molecules bind to the non-sex specific antigens in the fraction. A highly purified preparation of male bovine non-sex specific molecules can then be isolated and used to immunize rabbits etc. to obtain an antibody preparation highly specific for bovine non-sex specific molecules. Similarly, a highly purified preparation of female bovine non-sex specific molecules can be isolated and used to immunize rabbits etc. to obtain an antibody preparation highly specific for bovine non-sex specific molecules.

The substance which binds to non-sex specific molecules in the plasma membrane fraction, or parts thereof may be insolubilized to facilitate separation of the subfraction containing the conjugates of the substances and non-sex specific molecules, and the subfraction containing the sex-specific molecules. For example, the substance may be bound to a suitable carrier. Examples of suitable carriers are agarose, cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc.

The insolubilized substance may be prepared by reacting the material with a suitable insoluble carrier using known chemical or physical methods, for example, cyanogen bromide coupling.

The conjugates of substances and non-sex specific molecules are isolated from the subfraction containing sex specific molecules by conventional isolation techniques, for example, salting out, chromatography, electrophoresis, gel filtration, fractionation, absorption, polyacrylamide gel electrophoresis, agglutination, or combinations thereof. When the substance is insolubilized the conjugates may be eluted using conventional procedures.

In an embodiment of the invention, the sex specific molecules are isolated by molecular size and/or pI, using techniques known in the art. Electrophoresis according to standard practice as described in Sambrook, J. et al (Molecular Cloning A Laboratory Manual Cold Spring Harbour Laboratory Press, Sections 6.3–6.9, 1989 which is incorporated herein by reference) may be used to separate the sex specific molecules, and supports such as gel sheets or slabs, for example, polyacrylamide, agarose or other polymers are typically used as the supporting medium. Preferably, two dimensional gels which separate the proteins on the basis of two characteristics e.g. molecular size and pI are employed; most preferably SDS-polyacrylamide gel electrophoresis (IPG-SDS/PAGE), or immobilized pH gradient gel SDS-polyacrylamide gel electrophoresis (IPG-SDS/PAGE) are used to separate the sex specific molecules. The sex specific molecules may be eluted from the gels using conventional procedures such as described by Lee et al. (1987, Analyt. Biochem. 166:308).

II. CHARACTERIZATION OF MOLECULES IDENTIFIED USING THE METHOD OF THE INVENTION

Figure 1:
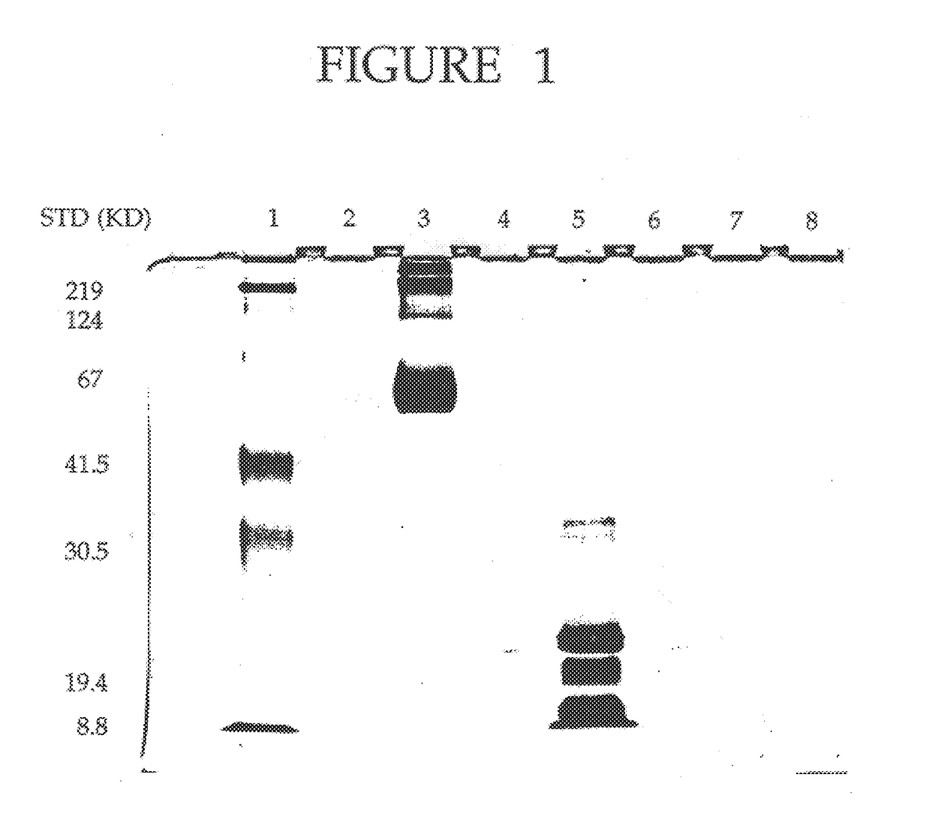
FIG. 1 is an SDS-PAGE gel showing purified fetal male (lane 3) and female (lane 5) proteins identified using the method of the invention.

The present inventor has identified male and female sex specific molecules using the methods described herein. As illustrated in FIG. 1, when male tissue is purified by the method of the invention specific protein molecules that are not present in the female material are located, and when female material is used different specific molecules are located which are not present in the male. For example, a sex specific protein has been identified in the male material which is characterized as being associated with the plasma membrane of male cells from bovine fetal and adult tissues, particularly the testes, spleen and kidneys. The molecule has a molecular weight on SDS-PAGE of about 60 KD.

The isolated and purified sex specific and non-sex specific molecules identified using the method of the invention may be used to isolate nucleic acid molecules having sequences which encode a sex specific or non-sex specific molecule. For example, the partial amino acid sequence may be determined for a sex specific or non-sex specific molecule, a DNA probe may be synthesized based on the amino acid sequence, and the probe may be used to screen a cDNA library of mRNA from a cell which produces the sex specific or non-sex specific molecule, or a genomic DNA library. Clones containing cDNA or genomic DNA hybridizing to the probes may be isolated, and cDNA or genomic DNA sequences encoding the molecules may be identified by for example, sequencing, or by expressing the cDNA in a eukaryotic expression system and identifying clones producing protein which binds to the antibody specific to the sex specific or non-sex specific molecules. The partial amino acid sequence may also be used to create primers for use in PCR to amply the gene encoding the sex specific or non-sex specific molecules. PCR-isolated genes may be sequenced and inserted into expression vectors for cloning.

Therefore, in accordance with an embodiment of the invention a purified and isolated nucleic acid molecule is provided containing a sequence encoding a sex specific or non-sex specific molecule of the invention.

Fragments of the nucleic acid molecules are contemplated by the present invention. In an embodiment, the fragments include fragments that have at least 15 bases, and which are capable of hybridizing to the nucleotide sequence encoding the sex specific or non-sex specific molecule under stringent hybridization conditions as described herein.

It will also be appreciated that a double stranded nucleotide sequence comprising a nucleic acid molecule of the invention or a fragment thereof, hydrogen bonded to a complementary nucleotide base sequence, and an RNA made by transcription of this nucleotide sequence are contemplated by the present invention.

Further, it will be appreciated that the invention includes nucleic acid or amino acid sequences which have substantial sequence identity. The term "sequences having substantial sequence identity" means those nucleic acid and amino acid sequences which have slight or inconsequential sequence variations, i.e. the sequences function in substantially the same manner to produce substantially the same polypeptides as the actual sequences. The variations may be attributable to local mutations, polymorphisms, or structural modifications.

Stringent hybridization conditions are those which are stringent enough to provide specificity, reduce the number of mismatches and yet are sufficiently flexible to allow formation of stable hybrids at an acceptable rate. Such conditions are known to those skilled in the art and are described, for example, in Sambrook, et al, (1989, Molecular Cloning, A Laboratory Manual, Cold Spring Harbor).

The invention further provides amino acid sequences for the sex specific and non-sex specific molecules of the invention and sequences which have substantial identity with the amino acid sequences. The invention still further provides peptides which are unique to the sex specific and non-sex specific molecules of the invention. Preferably, the peptides have at least 10 to 20 amino acids.

The nucleic acid sequences contained in the nucleic acid molecules of the invention or a fragment thereof, may be inverted relative to their normal presentation for transcription to produce antisense nucleic acid molecules. The antisense nucleic acid molecules may be constructed using chemical synthesis and enzymatic ligation reactions using procedures known in the art. The antisense nucleic acid molecules of the invention or a fragment of the antisense sequence, preferably containing at least 15 bases, may be chemically synthesized using naturally occurring nucleotides or variously modified nucleotides designed to increase the biological stability of the molecules or to increase the physical stability of the duplex formed with the mRNA or the gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

III. PREPARATION OF MOLECULES IDENTIFIED USING THE METHOD OF THE INVENTION

Nucleic acid molecules encoding the sex specific and non-sex specific molecules identified using the method of the invention, or fragments thereof, may be isolated and sequenced using the procedures described above or they may be constructed by chemical synthesis and enzymatic ligation reactions using procedures known in the art.

The sex specific and non-sex specific molecules of the invention, or isoforms or parts thereof, may be prepared using recombinant DNA methods. Accordingly, the nucleic acid molecules having a sequence which codes for a sex specific molecule, non-sex specific molecule, or fragments thereof may be incorporated in a known manner into an appropriate expression vector which ensures good expression of the molecules, or isoforms, or parts thereof. Possible expression vectors include but are not limited to cosmids, plasmids, or modified viruses, so long as the vector is compatible with the host cell used.

The invention therefore contemplates a recombinant molecule containing a nucleic acid molecule encoding a sex specific molecule or non-sex specific molecule identified using the method of the invention, or fragments thereof, and the necessary elements for the transcription and translation of the inserted sequence. Suitable transcription and translation elements may be derived from a variety of sources, including bacterial, fungal, viral, mammalian, or insect genes. Selection of appropriate transcription and translation elements is dependent on the host cell chosen, and may be readily accomplished by one of ordinary skill in the art. Examples of such elements include: a transcriptional promoter and enhancer or RNA polymerase binding sequence, a ribosomal binding sequence, including a translation initiation signal. Additionally, depending on the host cell chosen and the vector employed, other genetic elements, such as an origin of replication, additional DNA restriction sites, enhancers, and sequences conferring inducibility of transcription may be incorporated into the expression vector. It will also be appreciated that the necessary transcription and translation elements may be supplied by the native gene and/or its flanking regions.

The recombinant molecules may also contain a reporter gene which facilitates the selection of host cells transformed or transfected with a recombinant molecule of the invention. Examples of reporter genes are genes encoding proteins such as β-galactosidase, chloramphenicol acetyltransferase, and firefly luciferase. Transcription of the reporter gene is monitored by changes in the concentration of the reporter protein such as β-galactosidase, chloramphenicol acetyltransferase, or firefly luciferase. This makes it possible to visualize and assay for expression of recombinant molecules.

Recombinant molecules can be introduced into host cells via transformation, transfection, infection, electroporation etc. Methods for transforming transfecting, etc. host cells to express foreign DNA are well known in the art (see, e.g., Itakura et al., U.S. Pat. No. 4,704,362; Hinnen et al., PNAS USA 75:1929–1933, 1978; Murray et al., U.S. Pat. No. 4,801,542; Upshall et al., U.S. Pat. No. 4,935,349; Hagen et al., U.S. Pat. No. 4,784,950; Axel et al., U.S. Pat. No. 4,399,216; Goeddel et al., U.S. Pat. No. 4,766,075; and Sambrook et al. Molecular Cloning A Laboratory Manual, 2nd edition, Cold Spring Harbor Laboratory Press, 1989, all of which are incorporated herein by reference).

Suitable host cells include a wide variety of prokaryotic and eukaryotic host cells, including bacterial, mammalian, yeast or other fungi, viral, plant, or insect cells.

The sex specific molecules, non-sex specific molecules, or isoforms or parts thereof may also be prepared by chemical synthesis using techniques well known in the chemistry of proteins such as solid phase synthesis (Merrifield, 1964, J. Am. Chem. Assoc. 85:2149–2154) or synthesis in homogenous solution (Houbenweyl, 1987, Methods of Organic Chemistry, ed. E. Wansch, Vol. 15 I and II, Thieme, Stuttgart).

The sex specific molecules or non-sex specific molecules of the invention, or isoforms or parts thereof, may be conjugated with other molecules, such as proteins or polypeptides. Fusion proteins may be prepared by fusing, through recombinant techniques, a region of the sex specific or non-sex specific molecules or parts thereof, and a selected protein or marker protein with a desired biological function. Examples of proteins which may be used to prepare fusion proteins include cytotoxins and immunogenic proteins. They may also be conjugated to other specific molecules, including antibodies, to direct localization of the molecules to specific target sites. In addition the genes coding for the molecules may be inserted into expression vectors under the control of site-specific promoters, to target specific sites. Genetic constructs may also be made containing coding sequences for sex specific molecules and sequences for strongly immunogenic molecules, in order to improve the antigenicity of the molecules (Tao and Levy, 1993, Nature Vol. 362:755–758).

The present invention also contemplates a method for screening for epitopes of sex specific molecules that are presented by Major Histocompatibility Complex II molecules. This may be accomplished by isolating plasma membrane preparations of macrophage or monocyte cells that have been pulsed with a sex specific molecule, and isolating the epitopes using the antibodies specific for the sex specific molecules obtained by the methods described herein.

IV. APPLICATIONS FOR THE MOLECULES IDENTIFIED USING THE METHOD OF THE INVENTION

The nucleic acid molecules encoding the sex specific and non-sex specific molecules identified using the method of the invention, or fragments thereof, allow those skilled in the art to construct nucleotide probes for use in the detection of nucleotide sequences in biological materials. A nucleotide probe may be labelled with a detectable substance such as a radioactive label which provides for an adequate signal and has sufficient half-life such as $^{32}P$, $^{3}H$, $^{14}C$ or the like. Other detectable substances which may be used include antigens that are recognized by a specific labelled antibody, fluorescent compounds, enzymes such as lac Z, antibodies specific for a labelled antigen, and chemiluminescense. An appropriate label may be selected having regard to the rate of hybridization and binding of the probe to the nucleotide sequence to be detected and the amount of nucleotide available for hybridization. Labelled probes may be hybridized to nucleic acids on solid supports such as nitrocellulose filters or nylon membranes as generally described in Sambrook et al, 1989, Molecular Cloning, A Laboratory Manual (2nd ed.). The nucleotide probes may be used to detect genes that encode the sex specific or non-sex specific molecules identified using the methods of the invention.

The sex specific or non-sex specific molecules identified using the methods of the invention, or isoforms and parts thereof, may be used to prepare antibodies. Antibodies having specificity for the molecules may also be raised against proteins prepared by expressing nucleic acid molecules encoding the molecules in a host cell as described above.

Within the context of the present invention, antibodies are understood to include monoclonal antibodies, polyclonal antibodies, antibody fragments (e.g., Fab, and $F(ab')_2$ and recombinantly produced binding partners.

Polyclonal antibodies may be readily generated by one of ordinary skill in the art from a variety of warm-blooded animals such as horses, cows, various fowl, rabbits, goat, sheep, rabbits, mice, or rats. Briefly, a sex specific or non-sex specific molecule is utilized to immunize the animal through intraperitoneal, intramuscular, intraocular, intrasplenic implantation e.g. using nitrocellulose as a carrier, or subcutaneous injections, in conjunction with an adjuvant such as Freund's complete or incomplete adjuvant, or following conjugation or chemical modification to increase antigenicity. Following several booster immunizations, samples of serum are collected and tested for reactivity to the sex specific molecule. Particularly preferred polyclonal antisera will give a signal on one of these assays that is at least three times greater than background. Once the titer of the animal has reached a plateau in terms of its reactivity to the sex specific molecule, larger quantities of antisera may be readily obtained either by weekly bleedings, or by exsanguinating the animal.

Monoclonal antibodies may also be readily generated using conventional techniques (see Kohler and Milstein, Nature 256, 495–497, 1975 which is incorporated herein by reference; see also Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), Cold Spring Harbor Laboratory Press, 1988, which are also incorporated herein by reference).

Briefly, within one embodiment a subject animal such as a rat or mouse is injected with a sex specific or non-sex specific molecule. The molecule may be admixed with an adjuvant such as Freund's complete or incomplete adjuvant in order to increase the resultant immune response. Between one and three weeks after the initial immunization the animal may be reimmunized with another booster immunization, and tested for reactivity to the molecule. Once the animal has plateaued in its reactivity to the protein, it is sacrificed, and organs which contain large numbers of B cells such as the spleen and lymph nodes are harvested.

Cells which are obtained from the immunized animal may be immortalized by transfection with a virus such as the Epstein bar virus (EBV) (see Glasky and Reading, Hybridoma 8(4):377–389, 1989). Alternatively, the harvested spleen and/or lymph node cell suspensions are fused with a suitable myeloma cell in order to create a "hybridoma" which secretes monoclonal antibody. Suitable myeloma lines include, for example, NS-1 (ATCC No. TIB 18), and P3X63-Ag 8.653 (ATCC No. CRL 1580).

Following the fusion, the cells may be placed into culture plates containing a suitable medium, such as RPMI 1640, or DMEM (Dulbecco's Modified Eagles Medium) (RH Biosciences, Lenexa, Kansas), as well as additional ingredients, such as Fetal Bovine Serum (FBS, e.g., from Hyclone, Logan, Utah, or JRH Biosciences). Additionally, the medium should contain a reagent which selectively allows for the growth of fused spleen and myeloma cells such as HAT (hypoxanthine, aminopterin, and thymidine) (Sigma Chemical Co., St. Louis, Mo.). After about seven days, the resulting fused cells or hybridomas may be screened in order to determine the presence of antibodies which are reactive against the sex specific or non-sex specific molecule. A wide variety of assays may be utilized to determine the presence of antibodies which are reactive against a non-sex specific or sex specific molecule, including for example Countercurrent Immuno-Electrophoresis, Radioimmunoassays, Radioimmuno-precipitations, Enzyme-Linked Immuno-Sorbent Assays (ELISA), Dot Blot assays, Inhibition or Competition Assays, and sandwich assays (see U.S. Pat. Nos. 4,376,110 and 4,186,530; see also Antibodies: A Laboratory Manual, Harlow and Lane (eds.), Cold Spring Harbor Laboratory Press, 1988). Following several clonal dilutions and reassays, a hybridoma producing antibodies reactive against a non-sex specific or a sex specific molecule may be isolated.

Other techniques may also be utilized to construct monoclonal antibodies (see William D. Huse et al., "Generation of a Large Combinational Library of the Immunoglobulin Repertoire in Phage Lambda," Science 246:1275–1281, December 1989; see also L. Sastry et al., "Cloning of the Immunological Repertoire in Escherichia coli for Generation of Monoclonal Catalytic Antibodies: Construction of a Heavy Chain Variable Region-Specific cDNA Library," Proc Natl. Acad. Sci USA 86:5728–5732, August 1989; see also Michelle Alting-Mees et al., "Monoclonal Antibody Expression Libraries: A Rapid Alternative to Hybridomas," Strategies in Molecular Biology 3:1–9, Jan. 1990; these references describe a commercial system available from Stratacyte, La Jolla, Calif., which enables the production of antibodies through recombinant techniques).

Similarly, binding partners may also be constructed utilizing recombinant DNA techniques to incorporate the variable region of one gene and the constant region of another gene e.g. a non-human animal variable region and a human constant region. Within one embodiment, the genes which encode the variable region from a hybridoma producing a monoclonal antibody of interest are amplified using nucleotide primers for the variable region. These primers may be synthesized by one of ordinary skill in the art, or may be purchased from commercially available sources. Primers for mouse and human variable regions are available from Stratacyte (La Jolla, Calif.). These primers may be utilized to amplify heavy or light chain variable regions, which may then be inserted into vectors such as ImmunoZAP™ H or ImmunoZAP™ L (Stratacyte), respectively. These vectors may then be introduced into *E. coli* for expression. Utilizing these techniques, large amounts of a single-chain protein containing a fusion of the $V_H$ and $V_L$ domains may be produced (See Bird et al., Science 242:423–426, 1988). In addition, such techniques may be utilized to change a "murine" antibody to a "human" antibody, without altering the binding specificity of the antibody.

Once suitable antibodies or binding partners have been obtained, they may be isolated or purified by many techniques well known to those of ordinary skill in the art (see Antibodies: A Laboratory Manual, Harlow and Lane (eds.), Cold Spring Harbor Laboratory Press, 1988). Suitable techniques include peptide or protein affinity columns, HPLC or RP-HPLC, purification on protein A or protein G columns, or any combination of these techniques.

The specificity of antibodies or binding partners for sex specific or non-sex specific molecules may be confirmed by reacting with purified antigen preparations. For example, the specificity of antibodies for female sex specific antigens may be confirmed by reacting the antibodies with a tissue sample prepared from a parthenogenote which is free of male sex specific antigens.

In one embodiment of the invention, antibodies to male- or female-sex specific molecules associated with bovine cell membranes are raised by injecting the purified bovine sex specific molecules into an appropriate recipient animal of a different species, preferably rabbits, sheep and goats. Most preferably, the different species is the sheep or goat as they will provide an increased productivity (increased amounts of serum) and anti-male and anti-female antibodies raised in a different species will result in secondary antibodies that will not cross-react. Antibodies have been raised against the molecules shown in FIG. 1. Each band in the one-dimensional gel electrophoretogram shown in FIG. 1 likely represents more than one protein, as demonstrated by two-dimensional electrophoresis. The antibodies produced by each band are therefore oligospecific; that is, they have reactivity to a small number (e.g. three or four) different antigens. By using 2-dimensional electrophoresis, single molecules are preferentially isolated and monospecific antibodies produced. In particular, using 2-dimensional Western blotting, the most antigenic, sex specific, and avidly binding molecules are identified.

The polyclonal or monoclonal antibodies to sex specific molecules may be used to detect sex specific molecules, or isoforms or parts thereof, in embryos, various cells and tissues (e.g. sperm cells, spleen, kidney, ovary, and testes, extracts and cells), and biological materials (e.g. body fluids such as blood, urine, and blastocoelic fluid, and amniotic fluids). The antibodies may also be used to quantify the amount of a sex specific molecule, or an isoform or part thereof, in a sample in order to determine its role in particular cellular events or pathological states. In particular, the polyclonal and monoclonal antibodies of the invention may be used in immuno-histochemical analyses, for example, at the cellular and sub-subcellular level, to detect a sex specific molecule of the invention, to localise it to particular cells, tissues, embryos, and organisms and to specific subcellular locations, and to quantitate the level of expression.

The polyclonal or monoclonal antibodies to non-sex specific molecules may be used to detect and/or quantify non-sex specific molecules in cells, tissues, and biological materials. The antibodies may also be used to detect cells from a particular species in tissue culture and in hybridoma studies.

Direct methods may be employed in which the antibody is labelled with a detectable substance as described above. Indirect methods may also be employed in which the primary antigen-antibody reaction is amplified by the introduction of a second antibody, having specificity for the antibody reactive against the sex specific or non-sex specific antibody. By way of example, if the antibody having specificity against the sex specific molecule of the invention is a rabbit IgG antibody, the second antibody may be goat anti-rabbit immunoglobulin G labelled with a detectable substance as described herein.

Generally, an antibody of the invention may be labelled with a detectable substance and the sex specific and non-sex specific molecules of the invention may be detected based upon the presence of the detectable substance. Examples of detectable substances include various enzymes, fluorescent materials, luminescent materials, biotin, magnetic particles, micro- or macro-particles, and radioactive materials. Examples of suitable enzymes include horseradish peroxidase, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include radioactive iodine $I^{125}$, $I^{131}$ or tritium. Antibodies may also be coupled to electron dense substances, such as ferritin or colloidal gold, which are readily visualised by electron microscopy.

Radioactive labelled materials may be prepared by radiolabeling with $^{125}$I by the chloramine-T method (Greenwood et al, Biochem. J. 89:114, 1963), the lactoperoxidase method (Marchalonis et al, Biochem. J. 124:921, 1971), the Bolton-Hunter method (Bolton and Hunter, Biochem. J. 133:529, 1973 and Bolton Review 18, Amersham International Limited, Buckinghamshire, England, 1977), the iodogen method (Fraker and Speck, Biochem. Biophys. Res. Commun. 80:849, 1978), the Iodo-beads method (Markwell Anal. Biochem. 125:427, 1982) or with tritium by reductive methylation (Tack et al., J. Biol. Chem. 255:8842, 1980).

Known coupling methods (for example Wilson and Nakane, in "Immunofluorescence and Related Staining Techniques", W. Knapp et al, eds, p. 215, Elsevier/North-Holland, Amsterdam & New York, 1978; P. Tijssen and E. Kurstak, Anal. Biochem. 136:451, 1984) may be used to prepare enzyme labelled materials. Fluorescent labelled materials may be prepared by reacting the material with umbelliferone, fluorescein, fluorescein isothiocyanate, dichlorotriazinylamine fluorescein, dansyl chloride, derivatives of rhodamine such as tetramethyl rhodamine isothiocyanate, or phycoerythrin.

When labelled antibody is used, the sex specific and non-sex specific molecules can be detected by measuring the labelled antibody-antigen conjugates. The appropriate method of measuring the labelled conjugates is dependent upon the detectable substance employed. For example, if the labelling agent is an enzyme, the sex specific molecule may be detected using a proper enzyme substrate for colorimetric, luminescent or fluorescent systems. If the labelling agent is a fluorescent material, the presence of a sex specific molecule may be determined by fluorescence intensity, and if the labelling agent is a radioactive material, the sex specific molecule of the invention may be localized by radioautography. The results of radioautography may be quantitated by determining the density of particles in the radioautographs by various optical methods, or by counting the grains.

The antibody against a sex specific or non-sex specific molecule may be insolubilized by binding to a suitable carrier. Examples of suitable carriers are described herein. The insolubilized antibody may be prepared by reacting the material with a suitable insoluble carrier using known chemical or physical methods, for example, cyanogen bromide coupling.

The antibodies and antibodies labelled with a detectable substance as discussed above, may be used to detect the presence of sex specific and non-sex specific molecules in conventional assays such as ELISA, radioimmunoassays, inhibition or competition assays, sandwich assays, Dot Blot assays, Radioimmunoprecipitation, or histochemical tests.

By way of example, the antibodies may be used to detect a sex specific molecule in a cell, tissue or biological material in an inhibition assay in which extracts of the material to be tested are coated to a plate, the antibody is reacted with increasing amounts of antigen in a test solution, and the presence of antigen in the test solution is quantified in relation to the amount of inhibition occurring when the pretreated antibody is allowed to react with the coated antigen in the plate. In another sandwich method or capture assay, purified antibody against a sex specific molecule is bound to a plate, varying amounts of a putative source of antigen are introduced, the plate is washed and the amount of bound antigen is determined by use of biotin-conjugated antibody and avidin-biotinylated peroxidase indicator.

The antibodies and nucleic acid probes suitable for detecting sex specific and non-sex specific molecules may be packaged into convenient kits providing the necessary materials packaged into suitable containers. For example, such kits may include a series of antibodies against sex specific or non sex-specific molecules. The kits may also include suitable supports useful in performing the methods of the invention.

The antibodies, nucleic acid probes and kits of the present invention have many practical applications. Sex-specific molecules (i.e. male-specific molecules in males and female-specific molecules in females) identified using the methods described herein are present on the outer surface of the plasma membrane of many cells, including the cells on the outer surface of bovine embryos. By exposing embryos to specific antibodies to these sex specific molecules, it is possible to identify the sex of the embryos, for example using detectable substances that can be bound to the antibodies. Embryos selected in this way can be recovered, the antibody can be washed off, continued in vitro culture followed by transfer to cows can be done, and successful gestation can result.

Thus, the invention also broadly contemplates a method for differentiating between males and females comprising exposing an embryo or growth media of an embryo, to one or more antibodies specific for an epitope of a sex specific molecule identified using the methods of the invention, under conditions so that a conjugate forms between the antibodies and the sex specific molecule, and detecting the conjugates. The detection of a conjugate with antibody to a male specific molecule determines a male, and the detection of a conjugate with antibody to a female specific molecule determines a female. Anti-male and anti-female antibodies may be used separately, in combination, or sequentially to differentiate between males and females. The direct and indirect methods discussed above which are embodied in conventional assays such as ELISA, radioimmunoassays, or histochemical tests may be used to sex embryos.

Embryos which may be sexed using the methods described herein may be obtained from mammalian species including, bovine, dogs, cats, horses, swine, goats, and sheep, and non-mammalian animals including avian species, fish, and reptiles. In some of these animals, the females are heterogametic (whereas in mammals males are heterogametic) and therefore, some mammalian male sex specific molecules may be homologous to female sex specific molecules of some of these non-mammalian species, and vice versa.

The embryos may be in vitro or in vivo fertilized embryos, or parthenogenotes.

Embryos may be obtained using conventional techniques. For, example, embryos may be obtained from superovulated sheep, goats, and cattle. Sheep goats and cattle may be injected with FSH-P in descending divided doses at 12 hour intervals for about 3 days, followed by injection of a prostaglandin analogue (e.g. Ono-1052, Ono Pharma. Co. Ltd., Japan). Embryos may be collected laparoscopically from goats and sheep.

Bovine female embryos may be collect nonsurgically by flushing the uteri of superovulated donors at about 6 to 7 days after estrus and artificial insemination. The embryos may be cultured at 37° C. in 5% $CO_2$: 95% air for about six hours in 10% bCS-supplemented BMOC-3 media (Brinster, RL, 1972: Cultivation of the mammalian embryo. In: G. Rothblat, VJ Cristfalo (eds); "Nutrition and Metabolism of Cells in Culture," Vol. 2. New York: Academic Press, pp252–286).

Antibody specific for an epitope of a sex specific molecule identified using the methods of the invention, may be prepared using the methods described herein. The conditions which may be employed so that a conjugate forms between the antibody and the sex specific molecule are generally known in the art. The amount of antibody used to form the conjugate may be selected based on the type of antibody, and the properties of the sex specific molecule. The conjugates may be separated by conventional isolation techniques, for example, salting out, chromatography, electrophoresis, gel filtration, fractionation, absorption, polyacrylamide gel electrophoresis, agglutination, or combinations thereof.

The following three techniques or combinations thereof are preferably used for separating embryos:

a) A double antibody method. The embryos may be exposed to antibodies against one or more sex specific molecules, followed by fluorescein-labelled anti-gammaglobulin second antibody. Sequential use of anti-male and anti-female antibodies, followed by their respective antibodies may be used. This method allows for manual separation of labelled from unlabelled embryos.

b) The embryos may be separated based on their morphology when incubated with an antibody to a sex specific molecule, following the procedures set out in Utsumi et al., (1993, Mol. Reprod. Devel. 36:238). The antibodies may reversibly retard the growth of male but not female embryos when using anti-male antibody or vice versa when using anti-female antibody. The antibodies may also be used with or without additives , e.g. complement, to irreversibly suppress or to kill embryos of one sex, leaving substantially pure cultures of the other sex. This method also allows for manual separation.

c) Magnetic bead labelling. In this method, embryos are exposed to commercially available, microscopically small magnetic beads coated with appropriate antibodies (e.g. Olsaker et al., 1993, Anim. Genet. 24:311), in this case either male-specific or female-specific antibodies. Magnetic beads coated with commercially available goat anti-rabbit immunoglobulin may be added to embryos previously exposed to male specific or female specific antibodies. Alternatively, the beads may be coated, for example with anti-rabbit immunoglobulin and then with male-specific antibody, and placed directly in a suspension of embryos, in an appropriate glass dish. Because the sex-specific proteins are present on the epithelial cell-surface, male embryos will bind to the male specific antibody on the beads, while female embryos will not. The beads and attached embryos are then pulled to the side of the dish, using a magnet. Commercially available combinations of second antibody and avidinbiotin enhanced magnetic beads may also be used.

The sex of the separated embryos may be confirmed using known procedures such as chromosomal analysis and/or by DNA methods.

Sperm cell membrane proteins contain molecules that react with male-specific or female specific antibodies produced using the methods of the invention. The anti-male and anti-female antibodies reacted with different-sized proteins. The proteins that reacted with the male-specific antibody include one that is the same size (about 60 kilodaltons) as the major molecule identified in purified male fetal and embryonic protein preparations (FIG. 1), and the female antibody similarly reacts with a molecule of a size found in female tissue. These results suggest that the different molecules, male-specific and female-specific, are preferentially situated in the two classes of sperm, Y and X respectively.

Therefore, the present invention also contemplates a method for separating male and female determining sperm from native sperm which comprises incubating the native sperm with one or more antibodies against a sex specific molecule identified using the methods of the invention, to form conjugates between male or female determining sperm and the antibodies, and isolating the conjugates and sperm which have not bound to conjugates. The antibodies used in the method may be the antibodies against the sex specific molecules identified in adult, fetal and embryonic cells and tissues, or they may be antibodies against male- and female-specific molecules isolated from sperm cell plasma membrane preparations.

The antibodies against X- or Y-specific antigens may bind to and inactivate X- or Y-sperm respectively, and may prevent them from fertilizing an ovum. The sperm cells not bound by the antibodies may remain viable and active for fertilizing ova. Thus, the invention provides a method to produce a semen sample enriched in active X- or Y-sperm and thus capable of increasing the probability that offspring will be of a desired sex, or will or will not carry a gene for a sex-chromosome linked trait.

The magnetic bead method (e.g. as described by Olsaker et al., 1993, supra) may be used to separate putative X- and Y-sperm. The beads, coated, for example with male-specific antibody, may be placed in a suspension of the sperm-cells, in an appropriate glass dish. Because the sex-specific proteins are present in the sperm cell plasma membranes, the Y-sperm cells bind to the male specific antibody on the beads, while the X-sperm will not. The beads are then pulled to the side of the dish, using a magnet. Sperm cells of the two classes, those adhering to the beads (Y) and those not adhering (X), are recovered.

The following method may also be used to separate male and female determining spermatozoa. A native sperm preparation may be exposed to a first antibody that binds male specific molecules. The exposed sperm may be suspended together with a conjugate of a second antibody that binds exclusively to the first antibody and an immunoabsorbent substrate in a protein-free diluent to form a conjugate/sperm preparation whereby the male sperm are bound to the substrate. The male sperm may then be recovered from the substrate by specific binding of the substrate.

The methods for separating male and female sperm described herein minimize damage to the sperm by mechanical handling, so that the sperm have improved viability. The methods are also non-invasive; they do not require chemical binding to cellular internal structures; they involve minimal manipulation; they are inexpensive; there are minimal requirements for equipment or instrumentation; and, they are readily carried out by a person skilled in the art.

The antibodies against sex specific molecules identified using the methods of the invention may also be used to control the sex of progeny in vivo. For example, females may be immunized against X-sperm, Y-sperm or both using vaccines containing the sex specific antigens identified using the methods of the invention thereby increasing the probability of offspring of a certain sex or decreasing fertility altogether. The sex of an animal's (preferably mammal's) progeny may be controlled to produce more females or males by placing antibody against male-specific molecules or female specific molecules respectively, and complement in the uterus of a pregnant animal to kill male or female embryos.

Antibodies against an epitope of a sex specific molecule identified using the methods of the invention may also be conjugated with a cytotoxin which inactivates sperm. Thus, the cytotoxin may be specifically targeted to sperm. These preparations may therefore be useful as a contraceptive. Antibodies to the male and female specific molecules identified using the methods described herein may also be useful as a contraceptive by contacting sperm with both the anti-male and anti-female antibodies. Antisense sequences to the male and female specific molecules may also have utility as contraceptives.

The sex specific molecules identified using the methods of the invention may also be used to detect the presence of antibodies specific for the sex specific molecules in a sample.

The antibodies specific for sex specific molecules identified using the methods of the invention are also important in the medical field for prevention of lethal sex linked genetic diseases in humans. For example, the female specific antibodies may be used to produce a semen sample enriched in active X- or Y-sperm thus increasing the probability that offspring will or will not carry a gene for a sex chromosome linked trait.

Non-sex specific molecules identified using the methods described herein and antibodies against an epitope of such non-sex specific molecules, may be used as species specific allelic markers. For example, the molecules and antibodies may be used to detect contamination of tissue culture with an unidentified cell, and they may be used in somatic cell studies to identify human and/or murine chromosomes.

The following non-limiting examples are illustrative of the present invention:

EXAMPLES

Example 1

Procedure for isolating sex-specific molecules

Preparation of antibody

Antibodies were raised in partially inbred New Zealand White rabbits. After obtaining pre-immune (negative control) serum samples, 4 rabbits (2 males and 2 females) for each series of antibodies were immunized with male or female bovine material to produce the following four types of antiserum (see Table 1, below): female rabbit anti-male bovine (designated α), female rabbit anti-female bovine (β), male rabbit anti-female bovine (γ) and male rabbit anti-male bovine (δ). The antisera were collected by bleeding the rabbits. After characterization by ELISA the antisera were equilibrated by dialysis.

TABLE 1

DESIGNATION OF ANTISERUM TYPES

|  |  | RECIPIENT (Rabbit) | |
| --- | --- | --- | --- |
|  |  | Female | Male |
| ANTIGEN | Male | α | δ |
| (Bovine) | Female | β | γ |

Preparation of antigen

Adult and fetal bovine material was obtained from an abattoir. Embryonic material was prepared from in vitro fertilized (IVF) embryos, or in vivo, flushed embryos.

Plasma membrane preparations were made from male and female adult or fetal liver, spleen, kidney and gonadal material, or whole blastocysts. In early fetal material in which the sex is not evident from external examination, and in embryonic material, sex is diagnosed by cytogenetic analysis, using techniques developed by King et al, (1979, Vet. Sci. Commun. 3:51), or by using a Y-chromosome specific DNA probe (Wildeman, University of Guelph, Guelph, Canada, 1995).

Plasma membrane preparations were solubilized and equilibrated to a high performance liquid chromatography (HPLC) system by dialysis. Columns were prepared for affinity chromatography, using ultra-affinity silica support columns (Beckman) and, as ligands, preimmune male and female rabbit serum, and IgG fractions of antisera β (female anti-female) and δ (male anti-male). The solubilized and equilibrated crude antigen preparations were passed through the preimmune, and β and/or δ columns in sequence. The void volume contained the sex-specific antigen components. The ligand-bound material comprises non sex-specific components that can be eluted. Sex specific and non sex-specific fractions were re-equilibrated to Tris-buffered saline by dialysis, and then reconcentrated. The eluted and reconstituted non sex-specific fractions can be used to immunize animals, e.g. rabbits, to produce improved antisera against non-sex specific components of native antigen. These antisera called ββ and δδ are improved in that they do not contain antibodies to sex specific molecules, but they do contain antibodies to non-sex specific molecules. In contrast, although β and δ type sera contain mainly non-sex specific antibodies, they might contain some sex-specific antibodies, to the extent that sex specific antigen, though highly evolutionarily conserved may nevertheless differ slightly between species.

Sex specific antigen preparations were then passed through a gel filtration column (Sephadex G-200). The peak fraction was again passed through the β and δ columns, then reconcentrated. In some experiments the sample was also passed through a DEAE anion exchange column, which was then eluted. The eluate was concentrated and assayed by ELISA, SDS-PAGE and Western blotting. α and γ antisera were also cleared by reaction against female and male antigen respectively.

Example 2

Following the affinity chromatography and gel filtration procedures on adult or fetal material as described in Example 1, putative sex specific male and female molecules, i.e. molecules of specific sizes, as seen in 1D electrophoresis, that are present exclusively in the purified male samples and others that are present exclusively in the female samples were obtained (FIG. 1, left). Note the ~60 KD male specific molecule in FIG. 1.

Antibodies against partially purified male and female samples have been raised. Using purified antibodies raised against adult material, fetal antigens can be identified and, using these to raise anti-fetal antibodies, embryonic antigens have been isolated. The anti-adult antibodies reacted more strongly to adult material than to fetal, and corresponding differences occurred at the fetal to blastocyst level. Thus, raising antibodies to embryonic proteins may provide even better specificity of antigen-antibody reaction than already have been achieved. Preliminary evidence from Western blotting also suggests that the anti-male and anti-female antibodies detect the presence of their corresponding antigens in extracted sperm proteins.

The sex-specific molecules are repeatably identified in the SDS-PAGE gels, and are being extracted from gels for further study by two-dimensional electrophoresis and Western blotting to establish whether the single band seen on one-dimensional electrophoresis contains one or more sex-specific molecule. Individual sex-specific molecules will be used to raise monospecific antibodies, and for amino acid sequencing to derive a nucleotide sequence for PCR work.

Example 3

The technique for sexing embryos described herein makes use of antibodies, which can "target" specific molecules in the embryo in much the same way that antibodies to infectious bacteria defend the body by "targeting" bacterial molecules. Antibodies that can identify specific male molecules in male embryos and other antibodies that recognize female molecules of female embryos have been developed. X- and Y-bearing sperm cells may contain female and male-specific molecules respectively and they may react with these antibodies. Western blotting techniques permit testing to determine whether a preparation of sperm protein molecules contains any molecules that react with male-specific or female specific antibodies prepared in accordance with the invention. Sperm plasma membrane is isolated from freshly collected bull ejaculate, using nitrogen cavitation following high pressure exposure and explosive decompression to remove the membranes. Following homogenization and solubilization, the material is electrophoresed, and transferred to nitrocellulose by standard methods. Western blotting is performed with antibody types $\alpha$ and $\gamma$.

In preliminary experiments using only partially purified preparations, the results show that there are sperm proteins that react to both types of antibodies. Furthermore, the male- and female-specific antibodies react with different-sized proteins. Finally, the proteins that react with the male-specific antibody include one that is the same size (about 60 kilodaltons) as the major molecule identified in purified male fetal and embryonic protein preparations (See FIG. 1 and Example 2), and the female antibody similarly reacts with a molecule of a size found in female tissue. These initial results suggest that the different molecules, male-specific and female-specific, may be preferentially situated in the two classes of sperm, Y and X respectively.

To confirm that antibody to male molecules binds to the Y-bearing sperm and the female antibody to the X-sperm an established DNA-sexing technique (Dr. Alan Wildeman, University of Guelph, 1995) will be modified to use on sperm cells. A method has been developed for spreading sperm cells on a slide, in a manner suitable for in situ hybridization, using a Y-chromosome specific probe, followed by immunocytochemistry, using the antibodies against the sex specific molecules identified using the methods of the invention.

Example 4

In preliminary experiments, anti-male specific antibodies were found to inhibit the development of male embryos and anti-female antibodies were found to inhibit the development of female embryos. It appears that if anti-male antibody can achieve 80% diagnosis then anti-female serum should be able to sex 80% of the remainder, giving a total success rate of about 96%.

Example 5

The antibodies produced as described herein will be used to develop a method for separating the two classes of sperm cells. An established method for separating cells by use of antibodies will be used, as follows. Commercially available, microscopically small magnetic beads are coated with appropriate antibodies (Olsaker et al., 1993, Anim. Genet. 24:311), in this case either male-specific, female-specific or non-sex specific antibodies (or with secondary antibody e.g. goat anti-rabbit IgG). The beads, coated, for example with male-specific antibody, will be placed in a suspension of the sperm-cells, in an appropriate glass dish. Because the sex-specific proteins are present on the cell surface, the Y-sperm cells will then bind to the male specific antibody on the beads, while the X-sperm will not. The beads are then pulled to the side of the dish, using a magnet. Sperm cells of the two classes are recovered as those adhering to the beads (Y) and those not (X).

Sperm proteins, extracted from the outer cell membranes of sperm cells by a standard procedure, will be purified to isolate the male- and female-specific molecules, following the method as described in Example 1. As set forth in Example 1, the procedure is based on using antibodies that remove non-sex specific proteins, thus leaving sex-specific proteins intact. Antibodies to these purified sperm proteins will then be prepared; such antibodies are anticipated to act more specifically in detecting the different sperm cells than do the antibodies raised from fetal (or embryonic) sex specific molecules.

The same-sex sera, beta ($\beta$) and delta ($\delta$), are use to remove the non-sex specific proteins. These sera can achieve this because of the way they are prepared. When bovine tissue is injected into a rabbit, the rabbit produces antibodies to many of the molecules contained in the bovine tissue, because the rabbit's immune system "senses" that these molecules are foreign to the rabbit. However, the molecules that control sexual development are quite similar in all mammals, so a female rabbit's immune system does not treat bovine female sex molecules as foreign, and will not efficiently produce antibodies to these proteins. Therefore, the serum produced in a female rabbit by injecting female bovine material will contain antibodies to all the bovine molecules that are not sex-specific, but few if any antibodies to the sex-specific proteins. If this serum is then brought into contact with freshly prepared female tissue, the non-sex specific molecules in this tissue will bind to the antibodies, leaving the sex-specific molecules unbound. Using the procedure of affinity chromatography, the bound molecules can be removed, leaving the female sex-specific proteins available for further purification, by the procedure of gel filtration. Similarly, using antibodies raised by male tissue in a male animal, purified male specific antigens are obtained.

The purified male- and female-specific proteins obtained from sperm protein will be used to produce new, specific antibodies. These are expected to be more efficient in the sperm-separation procedure.

Sperm-cells separated by the magnetic microbead procedure described above, will be tested for efficiency of separation. Initially this will be done by the in situ hybridization (DNA probe) technique. When good separation is achieved as judged by this means, in vitro fertilisation will be done. Ultimately, artificial insemination will be done as a field test of the efficiency of the procedure.

Example 6

Identification of Epitopes Presented by MHC class II Molecules

Macrophage or monoctye cells are harvested from rabbits and a short-term cell culture is established. After confluence of the cells the culture is pulsed with male or female antigen. Following processing and presentation of the immunodominant epitopes the cells are harvested and plasma membrane preparations are made. Because the association between presented antigen and the antigen presenting cells plasma membrane MHC molecules is very stable, Jensen, PE, J. Immunol. 143:420, 1989), the presented immunodominant epitopes can be recovered in this way. Following SDS-PAGE and Western blotting, α or γ antisera are used to identify sex-typical molecules, which are extracted and eluted from gels in parallel.

Example 7

Antisera of the γ (gamma) type (i.e. antisera against female bovine antigen molecules, raised in male rabbits) were used in conjunction with commercially available complement, to selectively kill female embryos and obtain a pure culture of males. In some experiments the enzyme pronase was also used, to explore whether this enzyme might facilitate passage of the antibody and/or complement through the sona pellucida, a covering membrane which surrounds the embryo at the stage studied. Pronase appeared to have no effect, and results of the experiments with and without pronase were therefore pooled. Other control experiments were also performed.

In the pooled data from experiments designed to obtained male embryos, of those embryos in which the sex could be unequivocally determined by chromosome analysis, 120 out of 129 such embryos studied consecutively were male. This gives a correct prediction rate of about 93%. The binomial theorem provides a standard statistical procedure for determining the probability of obtaining such a result by chance alone.

The data illustrates how the method of the invention makes it possible to isolate sex specific molecules, produce specific antibodies to these molecules and use these antibodies to select embryos by sex.

Example 8

Antisera of the γ (gamma) type were used to select Y-bearing sperm cells. Sperm were suspended in serum free in vitro culture medium and exposed to the antibody. Following treatment the semen was filtered in a glass wool filter, and sperm in the filtrate was used to perform in vitro fertilization. Following culture, the sex of the embryos produced was determined by cytogenetic analysis, The results are shown in the following Table 2.

TABLE 2

| Expt # | Ab | Male | Female | Undiag |
|--------|-----|------|--------|--------|
| 1. 2/5.96 | 25 γIgG | 1 | 0 | 7 |
| 2. 23/5.96 | 25 γIgG | 9 | 0 | 4 |
| 3. 23/5.96 | 25 γIgG | 4 | 0 | 0 |
| 4. 23/5.96 | 23 γIgG | 5 | 4 | 0 |
| 5. 30/5.96 | 17 γIgG | 10 | 0 | 0 |
| 6. 13/6.96 | 17 γIgG | 8 | 0 | 1 |
| 7. 11/7.96 | 17 γIgG | 9 | 1 | 1 |
| 8. 8/8.96 | 25 γIgG | 28 | 1 | 16 |
| Total | | 74 (93%) | 6 | 30 |
| Total excl #4 | | 69 (97%) | 2 | 30 |

The successful results with sperm have been obtained using three different γ antibodies. The success rate is 93% and if one excludes the one unusual experiment (#4) it is 97%.

Having illustrated and described the principles of the invention in a preferred embodiment, it should be appreciated by those skilled in the art that the invention can be modified in arrangement and detail without departure from such principles. We claim all modifications coming within the scope of the following claims.

All publications, patents and patent applications referred to herein, are herein incorporated by reference in their entirety to the same extent as If each individual publication, patent or patent application was specifically and individually indicated to be incorporated by reference in its entirety.

We claim:

1. A method for separating sex specific molecules and non-sex specific molecules associated with animal plasma membranes, comprising:

(a) treating a plasma membrane fraction from adult, fetal, or embryonic animal cells or tissues, with one or more antibodies which bind to non-sex specific molecules in the cell membrane fraction to form conjugates between the non-sex specific molecules and the antibodies; and (b) separating the material in the cell membrane fraction which does not bind to the antibodies to obtain a subfraction containing sex specific molecules.

2. A method according to claim 1, further comprising separating the antibodies from the conjugates to obtain a second subfraction containing non-sex specific molecules and isolating non-sex specific molecules in the second subfraction.

3. A method as claimed in claim 1 wherein the cell membrane fraction is obtained from a cell membrane of bovine cells.

4. A method as claimed in claim 1, wherein the one or more antibodies and female anti-female antibody and/or male anti-male antibody.

5. A method as claimed in claim 4 wherein the female anti-female antibody is produced by immunizing female animals of a first animal species with cell membrane fractions obtained from cells or tissues of females of a second animal species.

6. A method as claimed in claim 4 wherein the male anti-male antibody is produced by immunizing male animals of a first animal species with cell membrane fractions obtained from cells or tissues of males of a second animal species.

7. A method as claimed in claim 1, which further comprises preparing antibodies having specificity against an epitope of the sex specific molecule.

\* \* \* \* \*

UNITED STATES PATENT AND TRADEMARK OFFICE
Certificate

Patent No. 5,840,504

Patented: November 24, 1998

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Stan R. Blecher, Guelph, Canada; and Rosemarie Irene Howie, Ontario, Canada.

Signed and Sealed this Twenty-fifth Day of June 2002.

CHRISTINA CHAN
*Supervisory Patent Examiner*
Art Unit 1644